United States Patent [19]
Jachowicz et al.

[11] Patent Number: 6,008,359
[45] Date of Patent: Dec. 28, 1999

[54] PIPERIDINE ANTIOXIDANTS AND COMPOSITIONS THEREWITH FOR PREVENTING THE FADING OF ARTIFICIAL HAIR DYE

[75] Inventors: Janusz Jachowicz, Bethel, Conn.; Bruce C. Locke, Easton, Pa.; Ratan K. Chaudhuri, Lincoln Park, N.J.

[73] Assignee: ISP Investments Inc., Wilmington, Del.

[21] Appl. No.: 09/146,571

[22] Filed: Sep. 3, 1998

[51] Int. Cl.$^6$ .............................. D06P 5/02; C07D 211/36; C07D 211/56; C07D 211/26

[52] U.S. Cl. ........................ 546/242; 546/244; 546/246; 8/442

[58] Field of Search .................................. 546/242, 244, 546/246; 8/442

[56] References Cited

PUBLICATIONS

Kanno et al, Chemical Abstract vol. 107 No. 165597, "Optical information recording medium" (1993).
dimueller et al, Chemical Abstract vol. 123 No. 3 39753, "Prep. of bis(tetra–methyl piperidine)alkane as antioxidants @ light & heat stabilizer's" (1995).
Wiezer et al, Chemical Abstract vol. 91 No. 20338, "Sub. piperidinehydroxy–amides useful as light–protective agents" (1979).
Sumitomo et al, Chemical Abstract vol. 101 No. 56013, "Stabilized polyolefin comp." (1983).

*Primary Examiner*—John Kight
*Assistant Examiner*—Raymond Covington
*Attorney, Agent, or Firm*—Walter Katz; William J. Davis; Marilyn J. Maue

[57] ABSTRACT

Piperidine antioxidants and compositions therewith for preventing the fading of artificial hair dye are described herein.

6 Claims, No Drawings

PIPERIDINE ANTIOXIDANTS AND COMPOSITIONS THEREWITH FOR PREVENTING THE FADING OF ARTIFICIAL HAIR DYE

BACKGROUND OF THE INVENTION

1. Field of the Invention

This invention relates to compositions for preventing the fading of artificial hair dye, and more particularly, to a piperidine antioxidant for achieving this result effectively.

2. Description of the Prior Art

Hair comprises predominantly certain polypeptide chains that are held together by disulfide bonds that link adjacent polypeptide chains. These bonds are formed from two cysteine amino acid residues on the adjacent keratin polypeptides. The disulfide bonds impart mechanical strength and extensibility to the hair. However, exposure to sun tends to cause these disulfide bonds to break, predominantly on the outer surface of the hair and the outer surface of the hair cuticle. This effect makes the hair stiff and brittle in dry weather and frizzy in humid weather. The hair also loses its color and luster.

Photofilters or UV-absorbers have been employed in cosmetic products for many years to protect coloring dyes from photofading. Recently, sunscreens also have been added to hair care products to guard against the deleterious effects of solar irradiation on the hair.

Photoprotection of melanin in skin has been intensively investigated. For hair protection, several approaches have been described, such as the deposition of photofilters on the hair surface, and the use of antioxidants, or free radical scavengers. See W. P. Smith and F. J. Penna, U.S. Pat. No. 4,786,493.

Accordingly, it is an object of the present invention to provide new and improved compositions for preventing the fading of artificial hair dye on the hair of the user.

SUMMARY AND DESCRIPTION OF THE INVENTION

What is described herein is a composition for preventing the fading of artificial hair dye. The composition includes one or more of the following piperidine antioxidants:

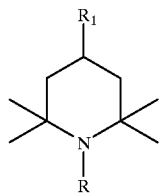

where:

R=H, CH$_3$, CH$_2$CH$_2$OH, COCH$_3$ or CH$_2$CH$_3$; and

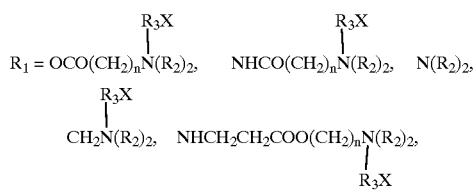

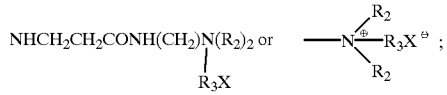

where:

R$_2$=C$_1$ to C$_4$ alkyl;

R$_3$=C$_1$ to C$_{30}$ alkyl (linear, branched, even or odd); and

X=is an anion, e.g. halide, methosulfate, tosylate or mesylate.

A preferred antioxidant is 4-dimethylamino-2,2,6,6-tetramethyl piperidine, preferably in the form of a quaternized compound, such as the dodecyl tosylate.

Preferably the composition of the invention includes the antioxidant compound in an amount of about 0.01–1% wt/wt.

The compositions of the invention can be used for skin treatment to slow down the oxidation of skin lipids and proteins, or to prevent oxidation of cosmetic ingredients in cosmetic formulations.

The invention will now be illustrated by the following examples.

EXAMPLE 1

Methyl Tosylate of 4-Dimethylamino-2,2,6,6-Tetramethyl Piperidine 10 g of 4-dimethylamino-2,2,6,6-tetramethyl piperidine is dissolved in 45 ml of isopropanol (IPA) and added 10 g of methyl tosylate. The resultant solution then is agitated and gradually heated to 110° C. to remove IPA. The reaction mixture is then maintained at 110° C. for 2 hours. Then 30 mm Hg vacuum is applied for 30 min. The residue obtained thereby then is recrystallized from a methyl ethyl ketone and ethanol mixture, washed and dried to give a white solid (90% yield).

EXAMPLE 2

4-Amino-2,2,6,6-Tetramethyl Piperidine

Aqueous solutions at a given concentration of the above compound were prepared as follows:

(A) 1% in deionized water;

(B) 0.5% in deionized water;

(C) 0.5% with 0.4% citric acid in deionized water, (pH 6.5).

A sample of 65% gray hair dyed with Clairol Nice'N Easy Auburn 112 showed a total color change of 5.51±0.29 after 40 hours irradiation. Samples treated with solutions (B) and (A) showed total color changes of only 4.49±0.49 and 3.25±0.60, respectively, after 40 hours irradiation. Solution (C) showed a total color change of only 4.53±0.27.

A sample of 65% gray hair dyed with Clairol Nice'N Easy Auburn 112 showed a total color difference between irradiated and unirradiated portions of the sample of 2.39 after 40 hours irradiation. Samples treated with solutions (B) and (A) showed color differences of only 1.02 and 2.03, respectively, after 40 hours irradiation.

EXAMPLE 3

4-Dimethylamino-2,2,6,6-Tetramethyl Piperidine

A sample of 65% gray hair dyed with Clairol Nice'N Easy Auburn 112 showed a total color difference between irradiated and unirradiated portions of the sample of 2.39 after 40 hours irradiation. Samples treated with 0.5% and 0.1% aqueous solutions of the above compound showed color differences of only 1.80 and 1.14, respectively, after 40 hours irradiation.

EXAMPLE 4

4-Dimethyldodecylammonium-2,2,6,6-Tetramethyl Piperidine Tosylate

The test solution comprised:

2% of the above compound

60% absolute ethanol;

38% deionized water.

Samples of Piedmont hair dyed with Clairol Nice'N Easy Auburn 112 showed a total color change of 19.18±1.14 after 37 hours irradiation. Samples treated with the test solution showed total color changes of only 17.42±2.53.

While the invention has been described with particular reference to certain embodiments thereof, it will be understood that changes and modifications may be made which are within the skill of the art. Accordingly, it is intended to be bound only by the following claims, in which:

What is claimed is:

1. A composition for preventing the fading of artificial hair dye which includes one or more of the following piperidine antioxidant compounds:

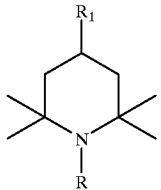

where:

$R=H$, $CH_3$, $CH_2CH_2OH$, $COCH_3$ or $CH_2CH_3$; and

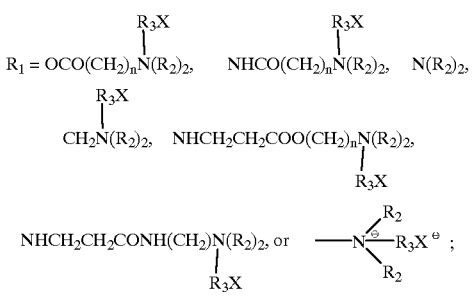

where:

$R_2=H$, $C_1$ to $C_4$ alkyl;

$R_3=C_1$ to $C_{30}$ alkyl (linear, branched, even or odd); and

X=an anion selected from halide, methosulfate, tosylate or mesylate, and n=an integer.

2. A composition according to claim 1 which is a solution.

3. A composition according to claim 1 which is an artificial hair dye formulation.

4. A composition according to claim 1 wherein said compound is present in an amount of about 0.01–1% by wt.

5. Methyl tosylate of 4-dimethylamino-2,2,6,6-tetramethyl piperidine.

6. 4-Dimethyldodecylammonium-2,2,6,6-tetramethyl piperidine tosylate.

* * * * *